(12) United States Patent
Pregesbauer

(10) Patent No.: US 10,345,284 B2
(45) Date of Patent: Jul. 9, 2019

(54) GROUND SENSOR

(71) Applicant: Geoprospectors GmbH, Traiskirchen (AT)

(72) Inventor: Michael Pregesbauer, Baden (AT)

(73) Assignee: Geoprospectors GmbH, Traiskirchen (AT)

( * ) Notice: Subject to any disclaimer, the term of this patent is extended or adjusted under 35 U.S.C. 154(b) by 0 days.

(21) Appl. No.: 15/781,027

(22) PCT Filed: Jul. 25, 2016

(86) PCT No.: PCT/EP2016/067651
§ 371 (c)(1),
(2) Date: Jun. 1, 2018

(87) PCT Pub. No.: WO2017/092885
PCT Pub. Date: Jun. 8, 2017

(65) Prior Publication Data
US 2018/0299422 A1 Oct. 18, 2018

(30) Foreign Application Priority Data
Dec. 2, 2015 (AT) .............................. A 51039/2015

(51) Int. Cl.
*G01N 33/24* (2006.01)
*A01B 79/00* (2006.01)
(Continued)

(52) U.S. Cl.
CPC ............. *G01N 33/24* (2013.01); *A01B 76/00* (2013.01); *A01B 79/005* (2013.01);
(Continued)

(58) Field of Classification Search
CPC . G01V 3/08; G01V 3/15; G01V 3/165; G01V 3/17; G01V 11/00; G01N 33/24; G01N 2033/245; G01N 27/025
See application file for complete search history.

(56) References Cited

U.S. PATENT DOCUMENTS 6,082,466 A 7/2000 Gudat
7,443,154 B1 10/2008 Merewether et al.
(Continued)

FOREIGN PATENT DOCUMENTS

CA 720967 A 11/1965
DE 202004011921 U1 10/2004
EP 1241488 A2 9/2002

OTHER PUBLICATIONS

International Preliminary Report on Patentability Application No. PCT/EP2016/067651 dated Feb. 28, 2018 7 pages.
(Continued)

*Primary Examiner* — Huy Q Phan
*Assistant Examiner* — Dustin R Dickinson
(74) *Attorney, Agent, or Firm* — Whitmyer IP Group LLC

(57) ABSTRACT

A device for surveying the condition of a substrate, in particular a soil sensor, having at least one transmitting coil and at least one, preferably four, receiving coils. The transmitting coil is arranged to generate an electromagnetic primary field and the receiving coil is arranged to receive the electromagnetic secondary field induced in the substrate by the primary field. The transmitting coil and the receiving coil are arranged in a housing which includes electromagnetic radiation shielding material. Also disclosed is an agricultural driven machine including a soil sensor and a method for operating a driven machine.

25 Claims, 6 Drawing Sheets

(51) Int. Cl.
*G01V 3/10* (2006.01)
*A01B 76/00* (2006.01)
*G01N 27/02* (2006.01)

(52) U.S. Cl.
CPC ............ *G01N 27/025* (2013.01); *G01V 3/10* (2013.01); *G01N 2033/245* (2013.01)

(56) References Cited

U.S. PATENT DOCUMENTS

| | | | | |
|---|---|---|---|---|
| 8,098,070 | B2* | 1/2012 | Lopez | G01V 3/15 |
| | | | | 324/337 |
| 2009/0201024 | A1* | 8/2009 | Bosnar | G01V 3/107 |
| | | | | 324/344 |
| 2011/0024657 | A1* | 2/2011 | Tower | F16K 37/0058 |
| | | | | 251/213 |
| 2013/0113648 | A1 | 5/2013 | Duvoisin, III et al. | |
| 2013/0128043 | A1* | 5/2013 | Avnery | A01D 34/008 |
| | | | | 348/148 |
| 2013/0197891 | A1* | 8/2013 | Jessop | G06T 17/05 |
| | | | | 703/9 |
| 2014/0097831 | A1 | 4/2014 | Whaley | |
| 2014/0139224 | A1* | 5/2014 | Stolarczyk | G01V 3/104 |
| | | | | 324/329 |
| 2014/0232408 | A1* | 8/2014 | Candy | G01V 3/104 |
| | | | | 324/329 |
| 2014/0329125 | A1* | 11/2014 | Miyanaga | B60R 13/0861 |
| | | | | 429/100 |
| 2015/0378051 | A1* | 12/2015 | Kapoor | G01N 27/02 |
| | | | | 324/334 |

OTHER PUBLICATIONS

International Search Report with Translation Application No. PCT/EP2016/067651 Completed: Oct. 10, 2016; dated Nov. 3, 2016 7 pages.

Jean-Michel Thomassin et al: "Polymer/carbon based composites as electromagnetic interference (EMI) shielding materials", Materials Science and Engineering: R: Reports, vol. 74, No. 7, Jul. 1, 2013; pp. 211-232.

Witten Opinion of the International Searching Authority Application No. PCT/EP2016/067651 Completed: Jul. 25, 2016; 6 pages.

* cited by examiner

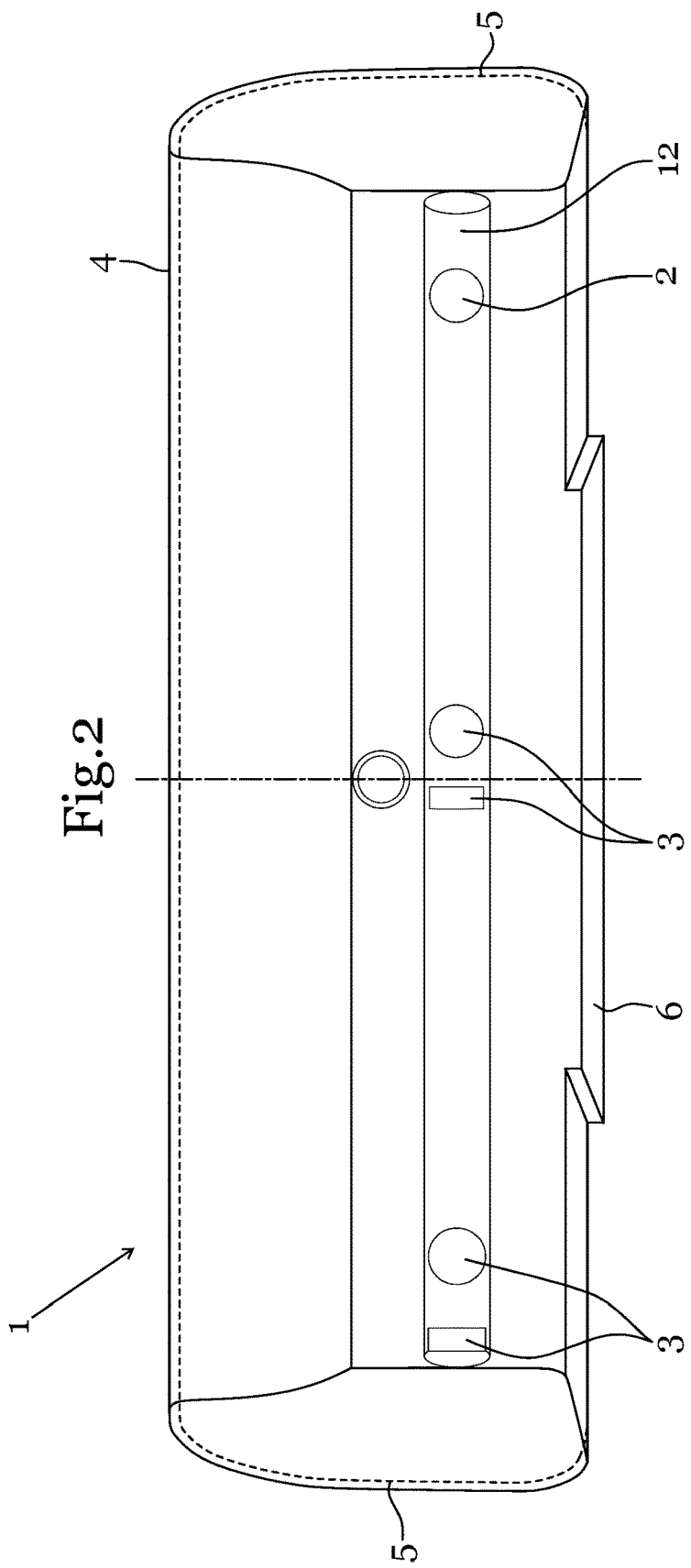

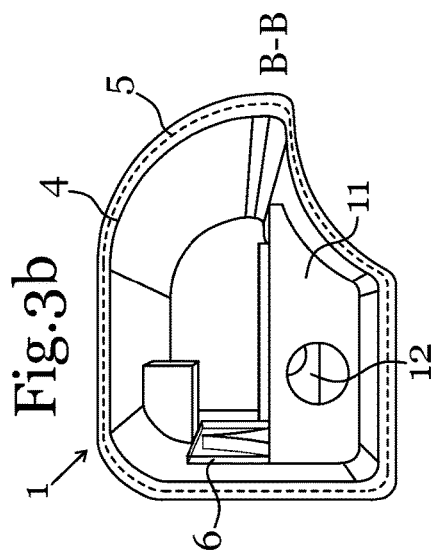
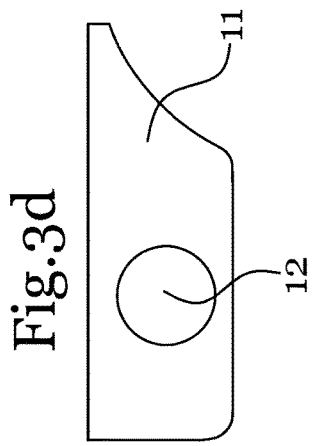
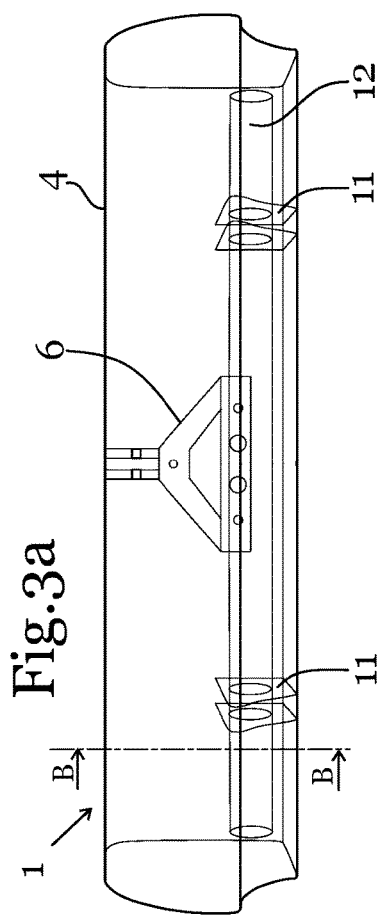
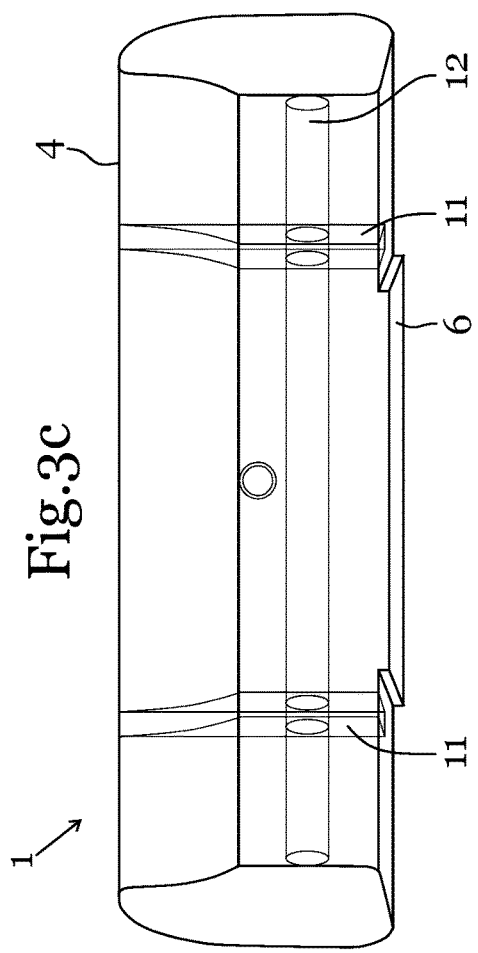

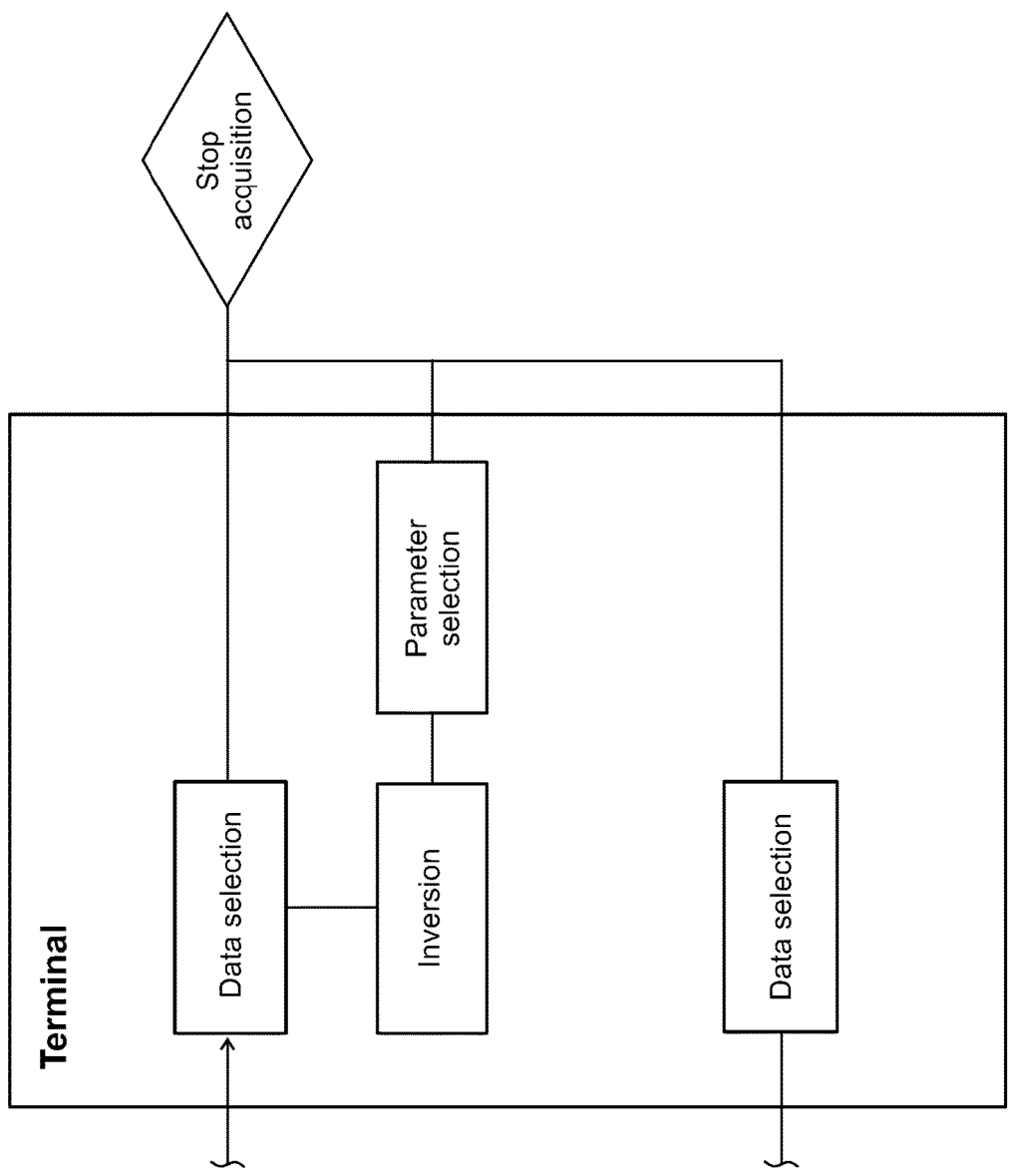

GROUND SENSOR

TECHNICAL FIELD

The present teaching relates to a device for surveying the condition of a substrate, an agricultural driven machine with such a device and a method for operating such an agricultural driven machine.

BACKGROUND

Using soil sensors which detect the condition of a substrate on the basis of electromagnetic induction (EMI) is known from the state of the art in the field of geophysics. In this case, a primary field is generated by an electromagnetic transmitting coil, which induces an electromagnetic secondary field in the substrate as a function of the soil condition, which is recorded and evaluated by one or more receiving coils in the surface region.

Conductivity values are derived from the signals of the receiving coils, from which values, depending on the configuration and sensitivity of the coils, the condition of the substrate, for example the density, the water saturation and the soil type, can be determined at a depth of a few cm to several meters.

Since, in contrast to other geophysical methods, EMI technology can be used in almost all substrate situations and is also relatively inexpensive to purchase, it has become established as a measuring method in precision farming. The main field of application of established systems is to survey soil inhomogeneities laterally in their own measurement runs and then to make them available to the farmer in the form of maps and plans.

In some cases, motorized systems are used, which are mounted on a usually specially constructed hitch system and pulled over the examination surface. In this case, a large distance of the soil sensor to the towing vehicle must be maintained in order to prevent as much as possible quality-reducing measurement noise or other errors in the data collection.

In the operation of known soil sensors, the data collection takes place independently of farmer's cultivation runs, since the operation of the system and the evaluation of the data requires specialized personnel. A complex process, in which the farmer is not involved, thus runs from the data acquisition to the delivery of the maps with the evaluated soil data.

Conventional devices are known, for example, from US 2013/113648 A1, US 2014/0097831 A1, DE 20 2004 011 921 U1, U.S. Pat. No. 7,443,154 B1 and EP 1 241 488 A2.

A device and a method for the analysis and the mapping of soil and terrain are known from the cited EP 1 241 488 A2, wherein the sensor is arranged in a box trailer, which is trailed behind a motorized vehicle.

SUMMARY

One object of the present teaching is to remedy the disadvantages of the existing systems and to realize a soil sensor and a method for operating a soil sensor, which enables the farmer to survey soil information flexibly and independently during the agricultural work run and this at the same time or subsequently to use for control of agricultural driven machines.

These and other objects are achieved by an agricultural driven machine and a method for operating the driven machine.

By arranging the transmitting coil and the receiving coils according to the present teaching in a housing which comprises electromagnetic radiation shielding material, it is ensured that the interference signals generated by the towing vehicle do not affect the measurement or only insignificantly, so that for the first time, it is possible to use the soil sensor during an agricultural work run.

An analysis of the soil condition is carried out in a known manner through the transmitting and receiving coils arranged in a cavity in the housing, wherein conductivity values of the substrate are determined. The determined conductivity values are used to determine the thickness of the first physically separable soil layer using 1D inversion. The 1D inversion is based on a Levenberg-Marquard inversion in which the data from a plurality of, preferably 4, independent receiving coils are inverted into depth values based on the accumulated response. Knowing the sensor position and orientation during EMI measurement is advantageous in order to be able to accurately determine the depth, since the accumulated response is height-dependent.

According to the present teaching, it can be provided that the housing comprises an electrically non-conductive composite, preferably a multi-layer glass fiber composite material. The housing can also be made of glass fiber reinforced plastic. This ensures that the enclosure is robust enough to meet the requirements of operating on a farm. According to the present teaching, it can also be provided that the housing—with the exception of the nonwoven fabric described below—entirely consists of this non-conductive composite.

According to the present teaching, it may be provided that the housing comprises an electromagnetic radiation shielding nonwoven fabric, which is preferably arranged in the entire housing wall except in the region below the coils. This nonwoven fabric serves to deflect the electromagnetic interference signals of the towing vehicle and other sources of interference, so that the coils arranged in the interior of the housing are not affected by the interference signals. In order not to weaken the actual measuring signals, the nonwoven fabric is not arranged in the region below the coils.

According to the present teaching, it can be provided that the nonwoven fabric comprises carbon-coated polyester and is arranged inside the housing wall, preferably between the layers of a multi-layer composite. Alternatively, the nonwoven fabric can also be mounted on the housing wall in the interior of the housing, for example, glued on it.

According to the present teaching, it can be provided that the nonwoven fabric has an electromagnetic attenuation in the low frequency range of 70 dB to 90 dB, preferably 80 dB, and a mechanical tensile strength in the longitudinal direction of 200 N/mm to 300 N/mm, preferably 260 N/mm. The term low frequency refers to a frequency of less than 2 Hz in this context.

According to the present teaching, it can be provided that the housing comprises a plurality, preferably six, glass filament fabric layers, wherein the nonwoven fabric is arranged between the glass filament fabric layers. Particularly preferred is an embodiment in which the housing comprises five inner glass filament fabric layers having a density of 280 g/m2 and an outer glass filament fabric layer having a density of 163 g/m2, wherein the nonwoven fabric is arranged between the second and the third layer.

According to the present teaching, it can be provided that the nonwoven fabric can be connected to an external grounding. For this purpose, a ground connection connected to the nonwoven fabric may be provided on the outer side of the housing.

The housing wall of the housing may have a thickness of less than 5 mm, preferably 4 mm. Due to the multi-layer structure of the housing wall described above, there is a sufficient mechanical stability of the housing in spite of the thin housing wall. According to the present teaching, it can be provided that the housing is hermetically sealed and the interior of the housing is protected against splashing water and contamination.

According to the present teaching, it can be provided that at least one distance sensor is provided for determining the distance of the device to the substrate. This makes it possible to ensure sufficient accuracy in the depth calculation based on the signals measured by the receiving coils. The distance sensor may be arranged in particular in the lower region of the housing.

According to the present teaching, it can be provided that the device comprises at least one inclination sensor for determining the inclination of the device relative to the substrate.

According to the present teaching, at least one localization module, preferably a GPS module, can be provided. This makes it possible to store the measured values determined by the soil sensor as a function of the specific position and thus to create a topological map of the soil condition. The GPS module can be arranged in or on the housing itself or also externally.

According to the present teaching, it may be provided that means for connecting an external computing unit and/or an external terminal are provided.

The present teaching further comprises an agricultural driven machine, in particular a towing vehicle such as a tractor, comprising a soil sensor and a computing unit for converting the signals received by the receiving coil into electrical conductivity values and ground parameters, for example density, humidity and soil type.

According to the present teaching, it can be provided that the computing unit is provided separately from the soil sensor, so that the soil sensor correspondingly, in particular also has wireless interfaces for the transmission of the measured signals of the receiver coils to the computing unit.

According to the present teaching, it can be provided that a terminal is provided for controlling the soil sensor. The terminal may in particular be arranged on the driven machine, for example, in the driver's cabin. Also, the above-mentioned GPS sensor according to the present teaching can be arranged on the driven machine and connected to the computing unit and/or the terminal.

According to the present teaching, it may be provided that the soil sensor is mounted on a front lifting mechanism of the driven machine.

Furthermore, it can be provided according to the present teaching that control outputs for controlling external soil cultivation equipment are provided on the driven machine.

The control outputs may preferably be arranged in the rear region of the driven machine, so that an immediate control of soil cultivation equipment arranged in the rear region of the driven machine is made possible based on the soil condition detected by the soil sensor during a work run.

The present teaching further extends to a method for operating an agricultural driven machine, wherein the ground parameters of the ground section to be currently processed are detected during a work run of the driven machine. This allows for the first time, the farmer to record the soil condition during a work run, for example, during sowing, and thus no separate step to examine the soil condition is required. The use of pre-recorded maps is therefore unnecessary for the farmer.

According to the present teaching, it may be provided that, for the calibration of the soil sensor, a one-time static measurement is first performed without a driven machine and a static offset is determined on the basis of the background noise detected in the static measurement, and the signals detected during the work runs are subsequently corrected for this static offset. The background noise may be, in particular, white noise which extends over the entire frequency range considered and has an amplitude of the conductance in the range of about 0.2 mS-0.4 mS.

This ensures that the static offset generated by the driven machine can be filtered out. This static offset is that offset which the measured data experiences through the running driven machine, as the soil sensor is mounted on the driven machine. The static offset is determined according to the present teaching by performing a static measurement in the same position and orientation once with and once without the driven machine. The difference between the two measurements is the static offset; this is determined once for a driven machine.

According to the present teaching, it can be provided that the detected signals are filtered by a filter, preferably a Hampel filter, during work runs in order to eliminate measurement errors and outliers. Instead of the Hampel filter, it is also possible to use any other filter which is suitable for detecting and removing outliers in the recorded measured values.

According to the present teaching, it can be provided that the signals detected during the work runs are filtered by an adaptive low-pass filter, wherein the parameters of the low-pass filter can be adjusted during the work run. This ensures that, in addition to the above-mentioned low-frequency background noise, high-frequency signal components can also be filtered. The filters can be implemented in particular as a software filter.

The cut-off frequency of the adaptive low-pass filter can be determined beforehand in an initialization phase and subsequently adjusted during a work run when a limit value of the amplitude of the measured signals is exceeded. This has the advantage in that the filter can be adapted to the changing conditions during the measurement. The detection of the changing conditions can be done, for example, by determining the amplitude of the measured signals over a wide frequency range before the filter, and continuously setting the cut-off frequency of the adaptive filter to the value at which the amplitude greatly increases above average, for example, at 5 to 10 times the value at low frequencies.

According to the present teaching, it can be provided that the soil sensor is moved during the work runs of the driven machine at a speed of preferably 15 km/h over the substrate to be examined, wherein the detected condition of the substrate, for example, the soil type, is directly used to control soil cultivation equipment mounted in the rear region of the driven machine. This has the advantage according to the present teaching in that the farmer can already adjust the soil cultivation to the condition of the soil during the ordering of the field.

According to the present teaching, all processes of soil survey take place automatically, so that the farmer only has to start the data collection. The combination of software, data collection hardware, and installation location allows the farmer to run an application during operation. All data and calculated information surveyed by the soil sensor are available at the control output within the tractor's processing speed, wherein a maximum speed is determined at which the length of the driven machine is sufficient to provide the computed data at the control output in real time.

According to the present teaching, it may be provided that a warning message is output during the work run, if the environmental conditions do not permit the surveying of the condition of the substrate.

According to the present teaching, it can be provided that the condition of the substrate is recorded and stored in a database in a first work run beforehand, for example, during sowing, and is used in a later work run for soil cultivation.

Further features of the present teaching will become apparent from the claims, the description of the figures and the drawings.

BRIEF DESCRIPTION OF THE DRAWINGS

FIG. 2 is a set representation of the soil sensor;
FIG. 3a-3d are schematic views of the soil sensor;
and
FIG. 4a-4c are schematic flow diagrams of the method for operating an agricultural driven machine.

DETAILED DESCRIPTION

Figure 1:
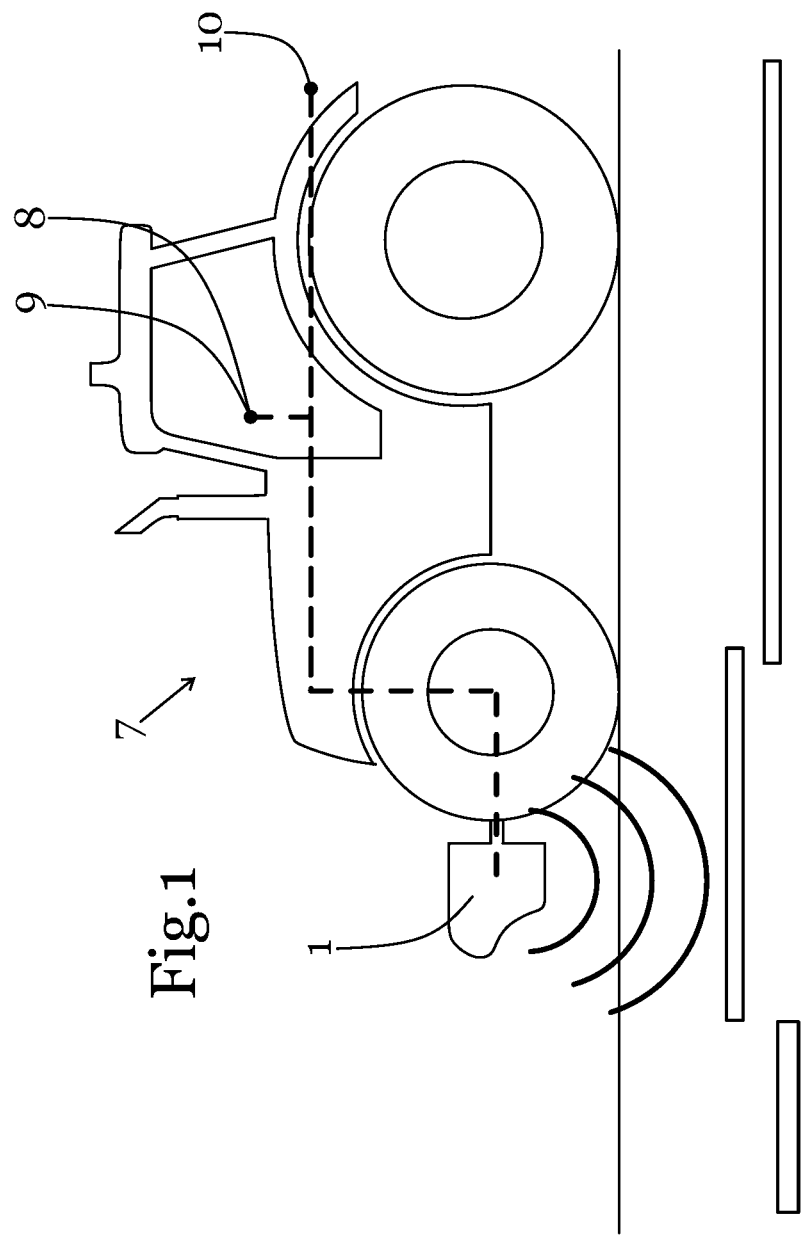
FIG. 1 is a set representation of a driven machine.

FIG. 1 shows a schematic representation of a driven machine 7 with a soil sensor 1 mounted on the front lifting mechanism. The signals measured by the soil sensor 1 are transmitted to a computing unit 8 in the driven machine 7 and evaluated there in order to detect the soil condition. In this case, the driven machine 7 is in motion, so that a region of the substrate can be continuously analyzed.

A terminal 9 for controlling the soil sensor 1 is also located in the region of the computing unit 8. Lines lead from the computing unit 8 or the terminal 9 to a control output 10 at the rear of the driven machine 7, which lines can be used to control soil cultivation equipment (not shown) with respect to the determined soil condition. A GPS receiver (not shown) connected to the computing unit 8 is further arranged at the rear of the driven machine.

FIG. 2 shows a schematic representation of the soil sensor 1 according to the present teaching in a view from above. This comprises a housing 4 made of a non-conductive material with a housing wall, in which a shielding, electrically conductive nonwoven fabric 5 is incorporated, which can be connected to the grounding of the driven machine 7 via grounding connection (not shown). The housing wall comprises a plurality of layers of a composite material of glass filament fabric, and the nonwoven fabric 5 is incorporated between the individual layers of the composite material.

A cavity 12 is located inside the housing 4, in which cavity a transmitting coil 12 and four differently oriented receiving coils 3 are arranged. The nonwoven fabric 5 is recessed in the region below the coils 2, 3 in order not to disturb the transmission and reception of the electromagnetic signals. A mounting device 6 is provided for fastening the soil sensor 1 on the front lifting mechanism of the driven machine 7. Brackets 11 (not shown in this illustration) are further located inside the housing 4 to stabilize the housing 4, which brackets have recesses for introducing the coils 2, 3.

FIGS. 3a-3c show further schematic views of the soil sensor 1 according to the present teaching. FIG. 3a shows the view of the soil sensor 1 from the front, FIG. 3b shows the soil sensor 1 from the side, and FIG. 3c shows the soil sensor 1 from above. The coils 2, 3 and the distance sensors are not shown in these schematic representations for reasons of clarity. The special shape of the housing 4 is visible in the sectional view following line B-B in FIG. 3b, which has a pronounced concave indentation at the front lower region. This prevents the movement of the soil sensor 1 over the substrate when obstacles such as stones or clods jam under the soil sensor 1 and hinder a measurement. In addition, the positioning of the nonwoven fabric 5 is shown schematically in FIG. 3b, which is arranged within the housing wall. In FIG. 3a, the mounting device 6 is shown schematically, which is located at the back side of the soil sensor 1.

FIG. 3d shows a view of a bracket 11, which for stabilization is arranged in the interior of the housing 4 and has a circular cavity 12 for receiving the coils 2, 3.

Figure 4A:
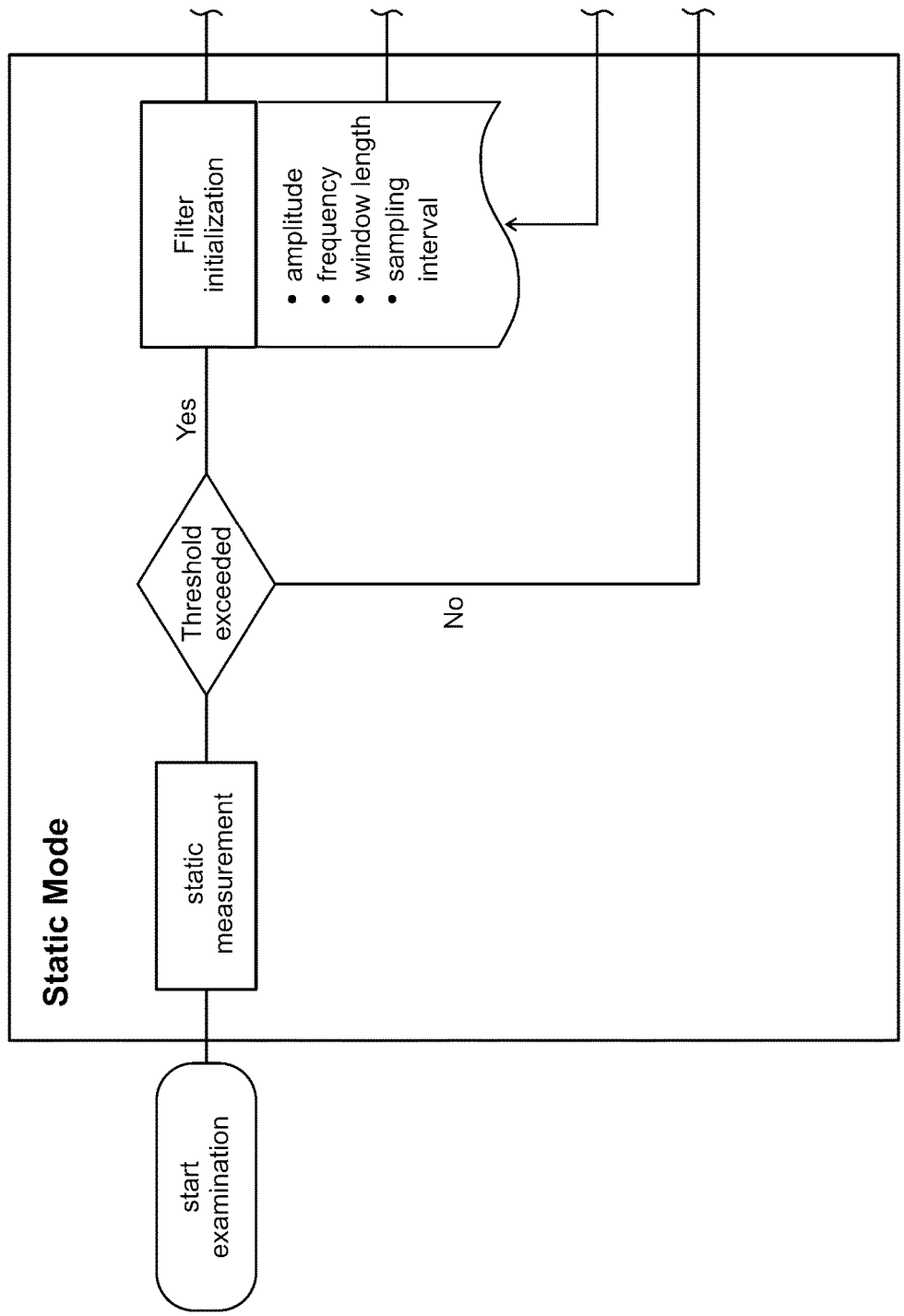
Figure 4B:
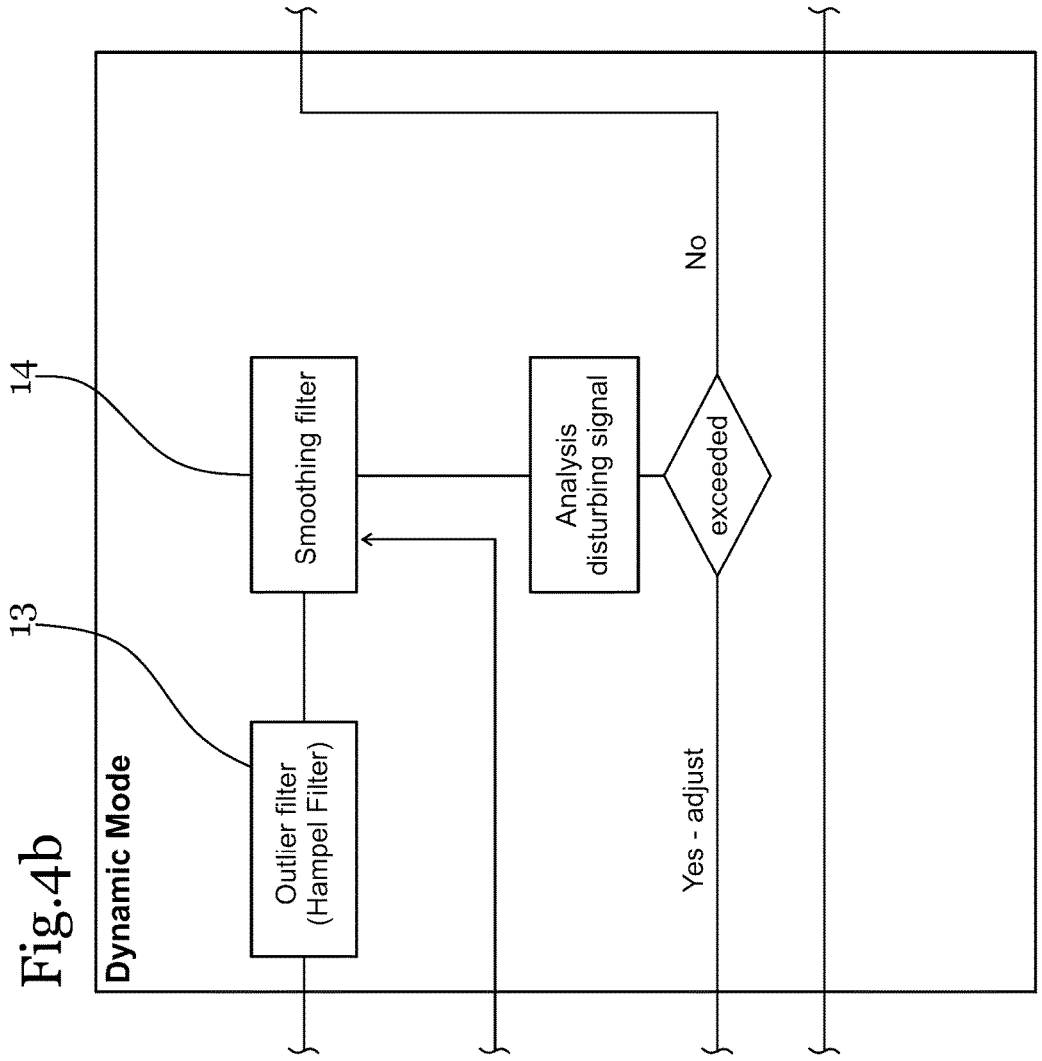

FIG. 4a-4c shows a schematic flow diagram of an embodiment of the method according to the present teaching for operating an agricultural driven machine with a soil sensor according to the present teaching.

A static initialization (static mode) of the system is performed before the actual measurement. In this case, two filters are initialized, namely on the one hand, a Hampel filter 13 for filtering outliers, and on the other hand, a smoothing filter 14, which is designed as a low-pass filter. During the measurement phase (dynamic mode), the measured conductivity values and the interfering signals are continuously analyzed (analysis noise) and the parameters of the smoothing filter are optionally adjusted via a feedback loop.

Finally, the calculation of the 1D inversion for determining the ground parameters from the conductivity values received by the four coils takes place at the terminal or the computing unit.

The invention claimed is:
1. An agricultural driven machine, comprising
a soil sensor for surveying the condition of a substrate,
wherein the soil sensor includes at least one transmitting coil and at least one receiving coil,
wherein the transmitting coil is arranged to generate an electromagnetic primary field and the at least one receiving coil is arranged to receive the electromagnetic secondary field induced in the substrate by the primary field,
wherein the transmitting coil and the at least one receiving coil are arranged in a housing which includes electromagnetic radiation shielding material,
wherein the soil sensor is mounted on a front lifting mechanism of the driven machine,
wherein during a work run of the driven machine, soil parameters of a soil section are detected,
wherein for calibration of the soil sensor, a static measurement without a driven machine is first performed and, based on background noise detected in the static measurement, a static offset is determined, and consequently, signals detected during the work run are corrected by the static offset.

2. The agricultural driven machine according to claim 1, wherein the housing includes an electrically non-conductive composite.

3. The agricultural driven machine according to claim 1, wherein the electromagnetic radiation shielding material comprises nonwoven fabric.

4. The agricultural driven machine according to claim 3, wherein the nonwoven fabric includes carbon-coated polyester and is arranged inside the housing wall.

5. The agricultural driven machine according to claim 4, wherein the nonwoven fabric has an electromagnetic attenuation of 70 dB to 90 dB in the low frequency range, and has a mechanical tensile strength in the longitudinal direction of 200 N/mm to 300 N/mm.

6. The agricultural driven machine according to claim 3, wherein the wall of the housing includes a plurality of glass filament fabric layers, wherein the nonwoven fabric is arranged between the glass filament fabric layers.

7. The agricultural driven machine according to claim 6, wherein the wall of the housing includes five inner glass filament fabric layers having a density of 280 g/m2 and an outer glass filament fabric layer having a density of 163 g/m2, wherein the nonwoven fabric is arranged between the second and the third layer.

8. The agricultural driven machine according to claim 3, wherein a grounding line electrically connected to the nonwoven fabric is provided to connect the nonwoven fabric to an external grounding of a driven machine.

9. The agricultural driven machine according to claim 1, wherein the housing wall of the housing of the soil sensor has a thickness of less than 5 mm.

10. The agricultural driven machine according to claim 1, wherein the housing of the soil sensor is hermetically sealed and the interior of the housing is protected against splashing water and contamination.

11. The agricultural driven machine according to claim 1, wherein at least one distance sensor for determining the distance of the device to the substrate is provided on the soil sensor.

12. The agricultural driven machine according to claim 1, wherein at least one inclination sensor for determining the inclination of the device relative to the substrate is provided on the soil sensor.

13. The agricultural driven machine according to claim 1, wherein at least one localization module, preferably a GPS module, is provided on the soil sensor.

14. The agricultural driven machine according to claim 1, wherein a device is provided for connecting an external computing unit and/or an external terminal to the soil sensor.

15. The agricultural driven machine according to claim 1, wherein a computing unit is provided for converting the signals received by the receiving coil into electrical conductivity values and soil parameters.

16. The agricultural driven machine according to claim 1, wherein a terminal is provided for controlling the soil sensor.

17. The agricultural driven machine according to claim 1 wherein control outputs are provided on the driven machine for controlling external soil cultivation equipment.

18. The agricultural driven machine according to claim 17, wherein the control outputs are arranged in the rear region of the driven machine, so that an immediate control of soil cultivation equipment arranged in the rear region of the driven machine is made possible based on the soil condition detected by the soil sensor during a work run.

19. A method for operating an agricultural driven machine, comprising providing an agricultural driven machine according to claim 1.

20. The method according to claim 19, wherein signals detected during the work run are filtered through a filter in order to eliminate measuring errors and outliers.

21. The method according to claim 19, wherein the signals detected during the work run are filtered by an adaptive low-pass filter, wherein the parameters of the low-pass filter can be adjusted during the work run.

22. The method according to claim 21, wherein the cut-off frequency of the low-pass filter is set in an initialization phase and is adjusted during a work run when exceeding a limit value of the amplitude of the measured signals.

23. The method according to claim 19, wherein the soil sensor is moved during the work run of the driven machine at a speed of at most 15 km/h over the substrate to be examined, wherein the detected condition of the substrate is used to directly control soil cultivation equipment mounted at the rear region of the driven machine.

24. The method according to claim 19, wherein a warning message is output if the environmental conditions do not allow a surveying of the condition of the substrate.

25. The method according to claim 19, wherein the condition of the substrate is recorded in a first work run beforehand and is stored in a database and is used in a later work run for soil cultivation.

* * * * *